(12) United States Patent
Jungwirth et al.

(10) Patent No.: US 10,145,792 B2
(45) Date of Patent: *Dec. 4, 2018

(54) MULTI-CELL APPARATUS AND METHOD FOR SINGLE ION ADDRESSING

(71) Applicant: Honeywell International Inc., Morris Plains, NJ (US)

(72) Inventors: Matthew Edward Lewis Jungwirth, Golden Valley, MN (US); James Goeders, Plymouth, MN (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/412,857

(22) Filed: Jan. 23, 2017

(65) Prior Publication Data

US 2017/0122868 A1    May 4, 2017

Related U.S. Application Data

(63) Continuation of application No. 14/686,553, filed on Apr. 14, 2015, now Pat. No. 9,588,047.

(51) Int. Cl.
| | |
|---|---|
| *G01J 1/58* | (2006.01) |
| *G01N 21/64* | (2006.01) |
| *H01J 49/42* | (2006.01) |
| *F25B 23/00* | (2006.01) |
| *G06N 99/00* | (2010.01) |

(52) U.S. Cl.
CPC ......... *G01N 21/6404* (2013.01); *F25B 23/00* (2013.01); *G01N 21/64* (2013.01); *G01N 21/6452* (2013.01); *G06N 99/002* (2013.01); *H01J 49/4205* (2013.01); *G01N 2021/6469* (2013.01); *G01N 2021/6484* (2013.01); *G01N 2201/067* (2013.01)

(58) Field of Classification Search
CPC ......... G01N 21/6452; G01N 2201/067; G01N 21/6404; G01N 2021/6484; G01N 2021/6469; G01N 21/64; H01J 49/4205; H01J 49/42
USPC ...................................... 250/459.1
See application file for complete search history.

(56) References Cited

U.S. PATENT DOCUMENTS

| | | | | |
|---|---|---|---|---|
| 5,527,731 A | * | 6/1996 | Yamamoto | ............ C23C 16/452 |
| | | | | 117/108 |
| 5,679,950 A | * | 10/1997 | Baba | .................. G01N 21/6404 |
| | | | | 250/281 |

(Continued)

OTHER PUBLICATIONS

Examination Report from related European Application No. 16154696.5, dated Jun. 26, 2017, 5 pages.

(Continued)

*Primary Examiner* — Taeho Jo
(74) *Attorney, Agent, or Firm* — Brooks, Cameron & Huebsch PLLC

(57) ABSTRACT

A multi-cell apparatus and method for single ion addressing are described herein. One apparatus includes a first cell configured to set a frequency, intensity, and a polarization of a laser and shutter the laser, a second cell configured to align the shuttered laser to an ion in an ion trap such that the ion fluoresces light and/or performs a quantum operation, and a third cell configured to detect the light fluoresced from the ion.

20 Claims, 3 Drawing Sheets

(56) References Cited

U.S. PATENT DOCUMENTS

| | | | |
|---|---|---|---|
| 6,489,609 B1* | 12/2002 | Baba | G01N 21/6404 |
| | | | 250/281 |
| 6,753,253 B1* | 6/2004 | Takahashi | H01J 37/304 |
| | | | 257/E21.295 |
| 7,180,078 B2 | 2/2007 | Pau et al. | |
| 7,859,350 B1 | 12/2010 | Schwindt et al. | |
| 2002/0145109 A1* | 10/2002 | Doroshenko | H01J 49/004 |
| | | | 250/287 |
| 2004/0007666 A1* | 1/2004 | Griffey | H01J 49/0077 |
| | | | 250/282 |
| 2004/0011952 A1* | 1/2004 | Johnston | G01N 27/622 |
| | | | 250/287 |
| 2006/0169914 A1* | 8/2006 | Holle | H01J 49/164 |
| | | | 250/423 P |
| 2006/0249670 A1 | 11/2006 | Monroe et al. | |
| 2007/0138386 A1* | 6/2007 | Makarov | H01J 49/0054 |
| | | | 250/288 |
| 2008/0296483 A1* | 12/2008 | McClelland | H01J 27/24 |
| | | | 250/251 |
| 2010/0316176 A1* | 12/2010 | Wood | G21G 1/10 |
| | | | 376/190 |
| 2011/0238316 A1* | 9/2011 | Ecker | C07H 21/04 |
| | | | 702/19 |
| 2013/0306855 A1* | 11/2013 | Raptakis | H01J 49/025 |
| | | | 250/282 |
| 2016/0118238 A1* | 4/2016 | Gordon | H01J 49/0013 |
| | | | 250/282 |

OTHER PUBLICATIONS

Barwood, G.P., et al. "Automatic laser control for a 88Sr+ optical frequency standard", Meas. Sci. Technol. 23 (2012) 9 pp., IOP Publishing Ltd. UK & US.

Brady, G.R., et al. "Integration of flourescence collection optics with a microfabricated surface electrode ion trap", Appl Phys B (2011), 103:801-808, 8 pp.

Noek, Rachel, et al., "Trapping and Cooling of 174Yb+ Ions in a Microfabricated Surface Trap", Journal of the Korean Physical Society, vol. 63, No. 4, Aug. 2013, pp. 907-913.

Search Report from related European application 16154696.5 dated Oct. 2, 2016 (11 pp.).

* cited by examiner

MULTI-CELL APPARATUS AND METHOD FOR SINGLE ION ADDRESSING

STATEMENT OF GOVERNMENT RIGHTS

This invention was made with Government support under contract: W911NF-12-1-0605, awarded by the U.S. Army. The Government has certain rights in this invention.

CROSS-REFERENCE TO RELATED APPLICATIONS

The present application claims priority to U.S. application Ser. No. 14/686,553, filed Apr. 14, 2015, the specification of which is herein incorporated by reference.

TECHNICAL FIELD

The present disclosure relates to a multi-cell apparatus and method for single ion addressing.

BACKGROUND

An ion trap can use a combination of electrical and magnetic fields to trap (e.g., capture) an ion (e.g., a positively or negatively charged atom or molecule). When an ion trapped in an ion trap is illuminated by a laser (e.g. when a laser beam is focused onto the ion in the trap), the ion may fluoresce light or perform a quantum operation. The light fluoresced from the ion can be detected by a detector.

Multiple ion traps can be formed on a chip (e.g., die). However, in previous approaches, each additional ion trap (e.g., each additional trapped ion) may necessitate additional structure (e.g., hardware) and/or space, including, for instance, additional lasers. For example, in previous approaches there may be a linear (e.g., one-to-one) relationship between the number of ions and the number of lasers (e.g., each additional ion may necessitate an additional laser).

Further, previous approaches may not be able to achieve single ion addressing or detecting. That is, previous approaches may not be able to individually address multiple ions such that the light fluoresced from only a single ion at a time can be detected by the detector.

DETAILED DESCRIPTION

Figure 1:
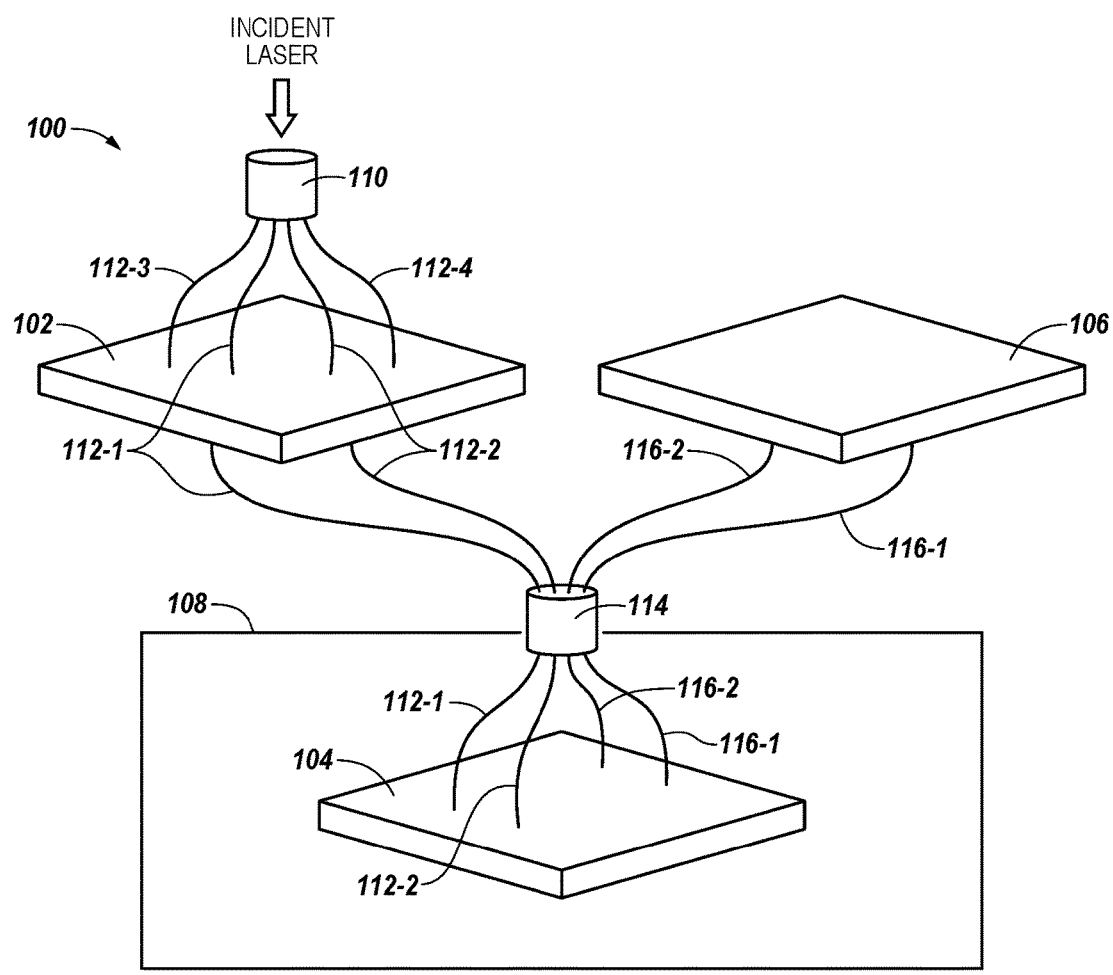
FIG. 1 illustrates an example apparatus for single ion addressing in accordance with one or embodiments of the present disclosure.

A multi-cell apparatus and method for single ion addressing are described herein. For example, one or more embodiments include a first cell configured to set a frequency, intensity, and a polarization of a laser and shutter the laser, a second cell configured to align the shuttered laser to an ion in an ion trap such that the ion fluoresces light and/or performs a quantum operation, and a third cell configured to detect the light fluoresced from the ion.

Embodiments in accordance with the present disclosure can achieve single ion addressing. That is, embodiments in accordance with the present disclosure can individually address multiple ions (e.g., ions trapped in multiple ion traps or zones of a single trap) such that the light fluoresced from only a single ion at a time can be detected by a detector.

Further, embodiments in accordance with the present disclosure may have a non-linear relationship between the number of trapped ions and the number of lasers needed for interacting with the ions. For example, in embodiments of the present disclosure, a single laser can be used to interact with multiple ions (e.g., a single laser can be used for multiple ions or ion traps).

As such, embodiments of the present disclosure can realize scalability in achieving single ion addressing. For example, embodiments of the present disclosure can achieve single ion addressing without using a significant amount of additional structure (e.g., hardware) and/or space as compared to previous approaches.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that mechanical, electrical, and/or process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits. For example, 104 may reference element "04" in FIG. 1, and a similar element may be referenced as 304 in FIG. 3.

As used herein, "a" or "a number of" something can refer to one or more such things. For example, "a number of lasers" can refer to one or more lasers.

FIG. 1 illustrates an example apparatus 100 for single ion addressing in accordance with one or embodiments of the present disclosure. As shown in FIG. 1, apparatus 100 can include a first cell (e.g., optical cell) 102, a second cell (e.g., optical cell) 104, and a third cell (e.g., optical cell) 106. That is, cells 102, 104, and 106 can be three separate cells. Cell 102 can be referred to as a preparation cell, cell 104 can be referred to as an alignment cell, and cell 106 can be referred to as a detection cell. As shown in FIG. 1, cells 102 and 106 can be outside a vacuum (e.g., vacuum chamber) 108, and cell 104 can be inside vacuum 108.

Cell 102 (e.g., the preparation cell) can set a frequency, intensity, and a polarization of a laser (e.g., a laser beam), and shutter the laser. In some embodiments, cell 102 may prepare the state of the laser, and in some embodiments, the state of the laser may already be prepared before the laser enters cell 102, as will be further described herein (e.g., in connection with FIGS. 2A and 2B). Cell 102 will be further described herein (e.g., in connection with FIGS. 2A and 2B).

In some embodiments, the laser may be a Doppler cooling laser (e.g., a laser used in a Doppler cooling mechanism), and in some embodiments the laser may be a quantum operation laser (e.g., a laser used in a quantum operation, such as Raman cooling, state preparation, photoionization, loading, and/or ion transitions, for instance). In both such embodiments, the laser may be a 369 nanometer (nm) laser for a ytterbium ion. However, embodiments of the present disclosure are not limited to a particular type of laser. For example, embodiments of the present disclosure may include different types or frequencies of lasers for different types of ions or different operations.

Cell 104 (e.g., the alignment cell) can align the shuttered laser to (e.g., focus the shuttered laser on) an ion trapped in an ion trap for interaction with the ion to cause, for example, the ion to fluoresce (e.g., emit) light and/or perform a quantum operation. Cell 104 can receive the light fluoresced from the ion. Cell 104 will be further described herein (e.g., in connection with FIG. 3).

In some embodiments, the ion in the ion trap can be a ytterbium (Yb) ion. However, embodiments of the present disclosure are not limited to a particular type of ion.

Cell 106 (e.g., the detection cell) can receive (e.g., collect) the light fluoresced from the ion from cell 104, and detect (e.g., measure) the light fluoresced from the ion. For example, cell 106 can include an array of photo-multiplier tubes that can detect the light (e.g., photons) fluoresced from the ion. However, embodiments are not limited to a particular type of detection cell.

As shown in FIG. 1, apparatus 100 can include a first fiber bundle 110 and a second fiber bundle 114. Fiber bundle 110 can split an incident laser into a plurality of components before the laser enters cell 102. For instance, fiber bundle 110 can split the laser into a plurality of fibers (e.g., wires) 112-1, 112-2, 112-3, 112-4 (e.g., each laser component can propagate through a different fiber) before the laser (e.g., the laser components) enters cell 102, as illustrated in FIG. 1. That is, the fibers split, and each fiber enters cell 102 separately, as illustrated in FIG. 1. Although the embodiment illustrated in FIG. 1 includes four fibers, embodiments of the present disclosure are not limited to a particular number of fibers.

As shown in FIG. 1, fiber bundle 114 can bundle (e.g., re-bundle) the plurality of fibers 112-1, 112-2, 112-3, and 112-4 after the laser (e.g., after the fibers) exits cell 102 and before the laser (e.g., before the fibers) enters vacuum 108. For clarity and so as not to obscure embodiments of the present disclosure, only fibers 112-1 and 112-2 are shown being bundled by fiber bundle 114 in FIG. 1. The laser (e.g., the bundled fibers) can then enter vacuum 108 through fiber bundle 114, as illustrated in FIG. 1.

After the laser (e.g., after the fibers) enters vacuum 108, fiber bundle 114 can split (e.g., re-split) the plurality of fibers 112-1, 112-2, 112-3, 112-4, as shown in FIG. 1. For clarity and so as not to obscure embodiments of the present disclosure, only fibers 112-1, and 112-2 are shown being split by fiber bundle 114 in FIG. 1. The laser (e.g., the re-split fibers) can then enter cell 104. That is, the fibers re-split, and each fiber enters cell 104 separately, as illustrated in FIG. 1.

The light fluoresced from the ion can exit cell 104 through one or more of an additional plurality of fibers (e.g., wires) 116-1, 116-2, as illustrated in FIG. 1. Although the embodiment illustrated in FIG. 1 includes two such additional fibers, embodiments of the present disclosure are not limited to a particular number of such additional fibers.

As shown in FIG. 1, fiber bundle 114 can bundle the additional plurality of fibers 116-1, 116-2, (e.g., the fiber(s) having the light fluoresced from the ion) before the light fluoresced from the ion (e.g., before the fibers) exit vacuum 114. After the light fluoresced from the ion (e.g., after the fibers) exits vacuum 108, fiber bundle 114 can split (e.g., re-split) the additional plurality of fibers 116-1, 116-2, as shown in FIG. 1. The light fluoresced from the ion (e.g., the re-split fibers) can then enter cell 106. That is, the fibers re-split, and each fiber enters cell 106 separately, as illustrated in FIG. 1.

Figure 2A:
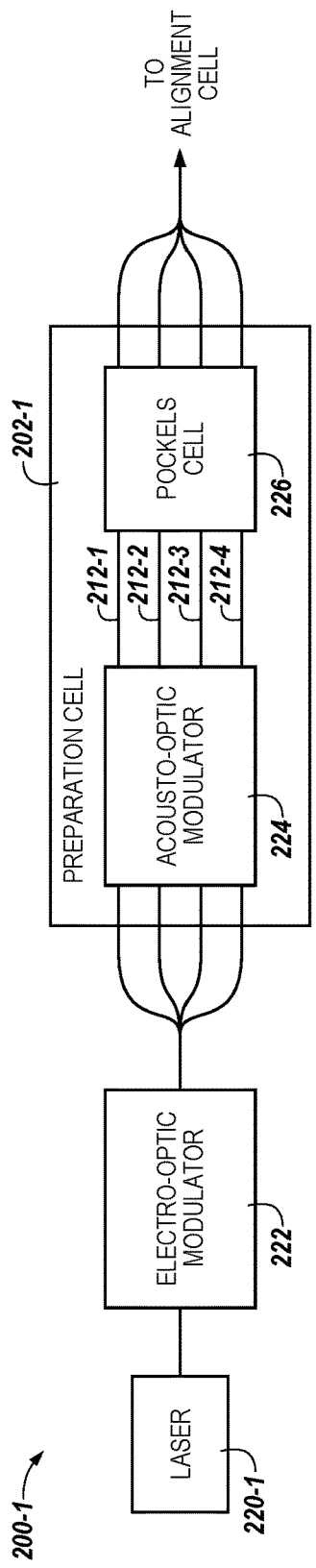
FIGS. 2A and 2B illustrate a portion of a preparation cell of an apparatus for single ion addressing in accordance with one or embodiments of the present disclosure.
Figure 2B:
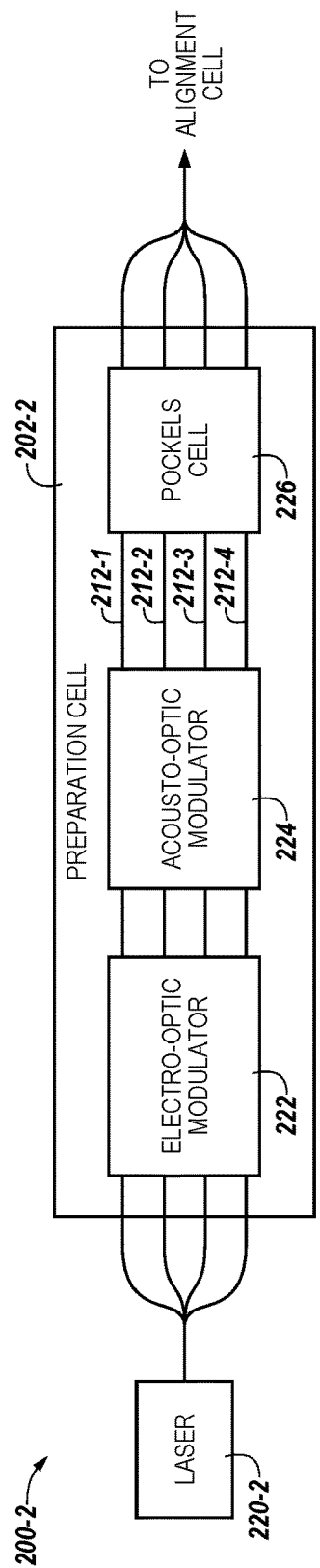

The number of ions a single laser can individually address using apparatus 100 may depend on three factors: the power of the illuminating laser, the laser power needed at the ion for the desired interaction, and the loss caused by the components within cell 102 that set the frequency, intensity, and polarization of the laser, shutter the laser, and prepare the state of the laser (e.g., the electro-optic modulator (EOM), the acousto-optic modulator (AOM), and the Pockels cell described in connection with FIGS. 2A and 2B). For example, the total transmission $T_{tot}$ in cell 102 can be given by:

$$T_{tot} = T_{EOM} T_{AOM} T_{Pockels} = 0.3 * 0.7 * 0.99 = 0.2$$

where $T_{EOM}$, $T_{AOM}$, and $T_{Pockels}$ are the estimated transmissions of the EOM, AOM, and Pockels cell, respectively. The power at the ion $\phi_{ion}$ can then be given by:

$$\phi_{ion} = T_{tot} \phi_{laser} = 0.2 * \phi_{laser}$$

where $\phi_{laser}$ is the power of the laser. The number of ions N that the laser can individually address can be given by:

$$N = \phi_{ion} / \phi_{required} = (0.2 * \phi_{laser}) / \phi_{required}$$

where clip $\phi_{required}$ is the laser power needed at the ion for the ion interaction. These equations can be solved to estimate the number of ions that can be simultaneously addressed.

FIG. 2A illustrates a portion of a preparation cell of an apparatus 200-1 for single ion addressing in accordance with one or embodiments of the present disclosure, and FIG. 2B illustrates a portion of a preparation cell of an apparatus 200-2 for single ion addressing in accordance with one or embodiments of the present disclosure. Apparatus 200-1 and/or apparatus 200-2 can be, for example, apparatus 100 previously described in connection with FIG. 1. For example, as shown in FIGS. 2A and 2B, apparatus 200-1 can include preparation cell 202-1, and apparatus 200-2 can include preparation cell 202-2. Preparation cell 202-1 and/or preparation cell 202-2 can be, for example, preparation cell 102 previously described in connection with FIG. 1.

As shown in FIGS. 2A and 2B, apparatus 200-1 includes a laser (e.g., incident laser) 220-1, and apparatus 200-2 includes a laser (e.g., incident laser) 220-2. Laser 220-1 can be a Doppler cooling laser (e.g., a laser used in a Doppler cooling mechanism), and laser 220-2 can be a quantum operation laser (e.g., a laser used in a quantum operation, such as Raman cooling, state preparation, photoionization, loading, and/or ion transitions, for instance). That is, the embodiment illustrated in FIG. 2A can include a Doppler cooling laser, and the embodiment illustrated in FIG. 2B can include a quantum operation laser. In both such embodiments, the laser may be a 369 nanometer (nm) laser. However, embodiments of the present disclosure are not limited to a particular type of laser.

As shown in FIGS. 2A and 2B, apparatuses 200-1 and 200-2 can each include an electro-optic modulator 222. In the embodiment illustrated in FIG. 2A, electro-optic modulator 220 is separate from (e.g., located outside of) preparation cell 202-1, and in the embodiment illustrated in FIG. 2B, electro-optic modulator 220 is included in (e.g., located within) preparation cell 202-2. In the embodiment illustrated in FIG. 2A, electro-optic modulator 222 may be a 7.37 GHz electro-optic modulator, and in the embodiment illustrated in FIG. 2B, electro-optic modulator 222 may be a 2.1 GHz electro-optic modulator. However, embodiments of the present disclosure are not limited to a particular type of electro-optic modulator.

In the embodiment illustrated in FIG. 2A, electro-optic modulator 222 can prepare the state of laser 220-1 (e.g., the state of a laser beam emitted by laser 220-1), and in the embodiment illustrated in FIG. 2B, electro-optic modulator 222 can prepare the state of laser 220-2 (e.g., the state of a laser beam emitted by laser 220-2). For example, electro-optic modulator 222 can generate large spacing sidebands for the state preparation, and address hyperfine transitions.

In the embodiment illustrated in FIG. 2A, electro-optic modulator 222 can prepare the state of laser 220-1 before the laser enters preparation cell 202-1. That is, in the embodiment illustrated in FIG. 2A, the state of the laser may already be prepared when the laser enters preparation cell 202-1.

For example, after electro-optic modulator 222 prepares the state of the laser, and before the laser enters preparation cell 202-1, the laser may split into a plurality of components (e.g., fibers) 212-1, 212-2, 212-3, 212-4 that separately enter preparation cell 202-1, as illustrated in FIG. 2A. That is, in the embodiment illustrated in FIG. 2A, electro-optic modulator 222 may be placed before preparation cell 202-1 and before the fiber split occurs. Because all the Doppler cooling beams may require the same frequency, locating electro-optic modulator 222 in such a manner can reduce the complexity of apparatus 200-1, as it may mean apparatus 200-1 may need only one electro-optic modulator (e.g., instead of needing a separate electro-optic modulator for each Doppler cooling beam). Components 212-1, 212-2, 212-3, and 212-4 can be, for example, fibers 112-1, 112-2, 112-3, 112-2 previously described in connection with FIG. 1.

Laser 220-1 may be split into components (e.g., fibers) 212-1, 212-2, 212-3, 212-4 by, for example, a fiber bundle (not shown in FIG. 2A), such as, for instance, fiber bundle 110 previously described in connection with FIG. 1. Although the embodiment illustrated in FIG. 2A includes four fibers, embodiments of the present disclosure are not limited to a particular number of fibers.

In the embodiment illustrated in FIG. 2B, electro-optic modulator 222 can prepare the state of laser 220-2 after the laser enters preparation cell 202-2. That is, in the embodiment illustrated in FIG. 2B, preparation cell 202-2 may prepare the state of the laser.

For example, the laser may split into a plurality of components (e.g., fibers) 212-1, 212-2, 212-3, 212-4 before the laser enters preparation cell 202-2 and before electro-optic modulator 222 prepares the state of the laser, such that each component separately enters preparation cell 202-1 and electro-optic modulator 222, as illustrated in FIG. 2B. That is, in the embodiment illustrated in FIG. 2B, electro-optic modulator 222 may be placed within preparation cell 202-2 and after the fiber split occurs.

For clarity and so as not to obscure embodiments of the present disclosure, a single electro-optic modulator 222 is illustrated in FIG. 2B. However, preparation cell 202-2 may include a separate electro-optic modulator for each component 212-1, 212-2, 212-3, 212-4 (e.g., component 212-1 may enter a first electro-optic modulator in preparation cell 202-2, component 212-2 may enter a second electro-optic modulator in preparation cell 202-2, etc.). As such, each electro-optic modulator may have individual control, and prepare the state, of each beam component, allowing for state preparation of individual quantum and giving each beam component the ability to set and interrogate ytterbium's hyperfine quantum states. Components 212-1, 212-2, 212-3, and 212-4 can be, for example, fibers 112-1, 112-2, 112-3, 112-2 previously described in connection with FIG. 1.

Laser 220-2 may be split into components (e.g., fibers) 212-1, 212-2, 212-3, 212-4 by, for example, a fiber bundle (not shown in FIG. 2B), such as, for instance, fiber bundle 110 previously described in connection with FIG. 1. Although the embodiment illustrated in FIG. 2B includes four fibers, embodiments of the present disclosure are not limited to a particular number of fibers.

As shown in FIGS. 2A and 2B, preparation cells 202-1 and 202-2 can each include an acousto-optic modulator 224. For instance, preparation cells 202-1 and 202-2 can include an individual (e.g., separate) acousto-optic modulator for each laser component 212-1, 212-2, 212-3, 212-4, in a manner analogous to the separate electro-optic modulators of preparation cell 202-2. In the embodiments illustrated in FIGS. 2A and 2B, acousto-optic modulator 224 can be 200 MHz acousto-optic modulator. However, embodiments of the present disclosure are not limited to a particular type of acousto-optic modulator.

In the embodiment illustrated in FIG. 2A, acousto-optic modulator 224 can set the frequency and intensity of laser 220-1 and shutter laser 220-1 (e.g., each separate acousto-optic modulator can set the frequency and intensity of and shutter its respective laser component 212-1, 212-2, 212-3, 212-4) after electro-optic modulator 222 prepares the state of laser 220. In the embodiment illustrated in FIG. 2B, acousto-optic modulator 224 can set the frequency and intensity of laser 220-2 and shutter laser 220-2 (e.g., each separate acousto-optic modulator can set the frequency and intensity of and shutter its respective laser component 212-1, 212-2, 212-3, 212-4) after electro-optic modulator 222 prepares the state of laser 220 (e.g., after each separate electro-optic modulator prepares the state of its respective laser component 212-1, 212-2, 212-3, 212-4). Light leakage from acousto-optic modulator 224 (e.g., from the shutter of the acousto-optic modulator) can be controlled using a radio-frequency (RF) switch (not shown in FIGS. 2A and 2B).

As shown in FIGS. 2A and 2B, preparation cells 202-1 and 202-2 can each include a Pockels cell 226 (e.g., a voltage-controlled wave plate). For instance, preparation cells 202-1 and 202-2 can include an individual (e.g., separate) Pockels cell for each laser component 212-1, 212-2, 212-3, 212-4, in a manner analogous to the separate electro-optic modulators of preparation cell 202-2.

In the embodiment illustrated in FIG. 2A, Pockels cell 226 can set the polarization of laser 220-1 (e.g., each separate Pockels cell can set the polarization of its respective laser component 212-1, 212-2, 212-3, 212-4) after acousto-optic modulator 224 sets the frequency and intensity of laser 220-1 and shutters laser 220-1. In the embodiment illustrated in FIG. 2B, Pockels cell 226 can set the polarization of laser 220-2 (e.g., each respective Pockels cell can set the polarization of its respective laser component 212-1, 212-2, 212-3, 212-4) after acousto-optic modulator 224 sets the frequency and intensity of laser 220-2 and shutters laser 220-2. For instance, Pockels cell 226 can be used to prevent electro-optic modulator 222 and/or acousto-optic modulator 224 from disturbing the polarization state of the laser since it is placed after these two devices.

As shown in FIGS. 2A and 2B, laser components 212-1, 212-2, 212-3, 212-4 may bundle (e.g., re-bundle) after exiting preparation cells 202-1 and 202-2, respectively. The bundled components (e.g., fibers) may then enter a vacuum (e.g., vacuum 108 previously described in connection with FIG. 1) and travel to an alignment cell (e.g., alignment cell 104 previously described in connection with FIG. 1). Laser components 212-1, 212-2, 212-3, 212-4 may be bundled by, for example, an additional fiber bundle (not shown in FIGS. 2A and 2B), such as, for instance, fiber bundle 114 previously described in connection with FIG. 1.

Figure 3:
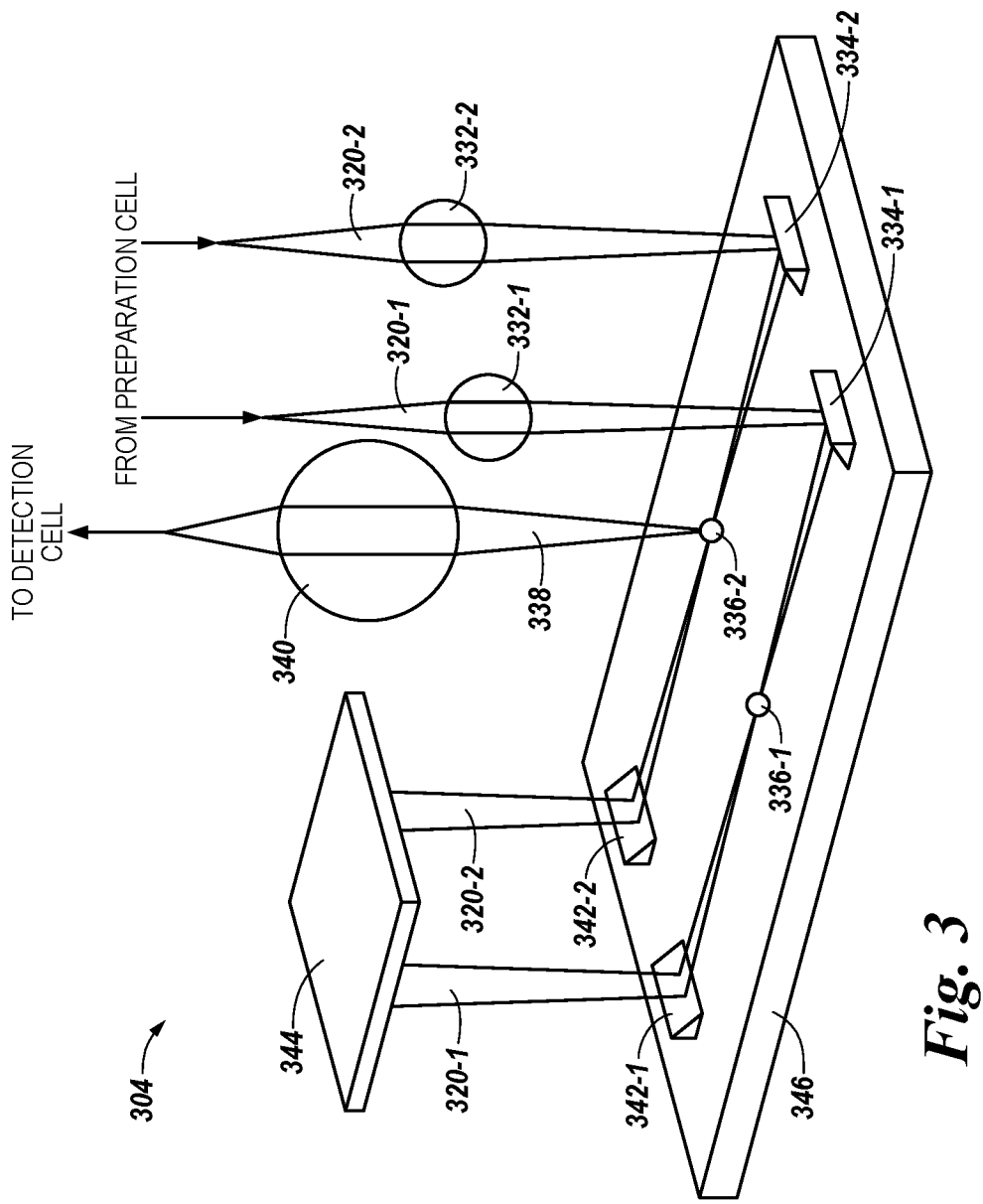
FIG. 3 illustrates a portion of an alignment cell of an apparatus for single ion addressing in accordance with one or embodiments of the present disclosure.

FIG. 3 illustrates a portion of an alignment cell 304 of an apparatus for single ion addressing in accordance with one or embodiments of the present disclosure. Alignment cell 304 can be, for example, alignment cell 104 of apparatus 100 previously described in connection with FIG. 1.

As shown in FIG. 3, a first component 320-1 and a second component 320-2 of a laser (e.g., laser beam) from a preparation cell (e.g., preparation cell 102 previously described in connection with FIG. 1) can enter alignment cell 304. For example, laser component 320-1 can enter (e.g. be input into) alignment cell 304 from a first fiber (e.g., fiber 112-1 previously described in connection with FIG. 1), and laser component 320-2 can enter alignment cell from a second fiber (e.g., fiber 112-2 previously described in connection with FIG. 1), as previously described herein (e.g., in connection with FIG. 1).

Laser component 320-1 can be a component of laser 220-1 previously described in connection with FIG. 2A, and laser component 320-2 can be a component of laser 220-2 previously described in connection with FIG. 2B. That is, in the embodiment illustrated in FIG. 3, laser component 320-1 can be a component of a Doppler cooling laser, and laser component 320-2 can be a component of a quantum operation laser. However, embodiments of the present disclosure are not limited to a particular type of laser.

As shown in FIG. 3, alignment cell 304 can include a first lens 332-1 and a second lens 332-2. Lenses 332-1 and 332-2 can be, for example, ball lenses. Further, the focal length of lenses 332-1 and 332-2 can be set to garner a particular beam waist and location for a given ion operation.

As shown in FIG. 3, lens 332-1 can focus laser component 320-1, and direct laser component 320-1 at mirror 334-1 formed (e.g., placed) on the surface of chip (e.g., die) 346. Lens 332-2 can focus laser component 320-2, and direct laser component 320-2 at mirror 334-1 formed on the surface of chip 346. The distance between the centers of lenses 332-1 and 332-2 and the surface of chip 346 can be, for example, three millimeters (mm).

As shown in FIG. 3, mirror 334-1 can direct (e.g., reflect) the focused laser component 320-1 at ion 336-1 trapped in an ion trap formed on chip 346, such that ion 336-1 is illuminated by focused laser component 320-1. Mirror 334-2 can direct the focused laser component 320-2 at ion 336-2 that may be trapped in an additional ion trap formed on chip 346, such that ion 336-2 is illuminated by focused laser component 320-2.

The distance between mirror 334-1 and ion 336-1, and the distance between mirror 334-2 and ion 336-2, can be, for example, 2.5 mm. The distance between ion 336-1 and 336-2 can be, for example, 0.5 mm. Ions 336-1 and 336-2 can be, for example, Yb ions. However, embodiments of the present disclosure are not limited to a particular type of ion.

As shown in FIG. 3, ion 336-2 may fluoresce (e.g., emit) light 338 and/or perform a quantum operation when illuminated by focused laser component 320-2. Fluoresced light 338 can be received (e.g., coupled) by lens 340 of alignment cell 304, as illustrated in FIG. 3. Lens 340 can be, for example, a ball lens having a diameter of 2 mm. Further, the focal length of lens 340 can be set to couple fluoresced light 338 into a fiber (e.g., output fiber) exiting alignment cell 304.

As shown in FIG. 3, fluoresced light 338 can exit alignment cell 304 after being received (e.g., coupled) by lens 340, and travel to a detection cell (e.g., detection cell 106 previously described in connection with FIG. 1). For example, fluoresced light 338 can exit (e.g. be output from) alignment cell 304, and travel to the detection cell, through a fiber (e.g., fiber 116-1 or 116-2 previously described in connection with FIG. 1), as previously described herein (e.g., in connection with FIG. 1).

As shown in FIG. 3, mirror 342-1 formed on the surface of chip 346 can direct (e.g., reflect) laser component 320-1 at beam dump 344 of alignment cell 304 after laser component 320-1 is aligned to (e.g., focused at), and illuminates, ion 336-1. Mirror 342-2 formed on the surface of chip 346 can direct laser component 320-2 at beam dump 344 after laser component 320-2 is aligned to, and illuminates, ion 336-2.

Laser components 320-1 and 320-2 can terminate at (e.g., upon reaching) beam dump 344. Terminating laser components 320-1 and 320-2 at beam dump 344 can mitigate stray light and/or heating in alignment cell 304.

Alignment cell 304 may be designed as a unit cell that can be repeated across an array (e.g., a 2D array) of ion traps formed on chip 346. That is, the embodiment illustrated in FIG. 3 can be repeated across an array of ion traps formed on chip 346. However, only one alignment cell 304 has been shown in FIG. 3 for clarity and so as not to obscure embodiments of the present disclosure.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. An apparatus for single ion addressing, comprising:
a first cell configured to:
set a polarization of a laser; and
shutter the laser; and
a second cell configured to align the shuttered laser to an ion in an ion trap such that the ion fluoresces light and/or performs a quantum operation.

2. The apparatus of claim 1, wherein the apparatus includes a third cell configured to detect the light fluoresced from the ion.

3. The apparatus of claim 1, wherein the first cell is configured to set a frequency of the laser.

4. The apparatus of claim 1, wherein the first cell is configured to set an intensity of the laser.

5. The apparatus of claim 1, wherein the second cell is inside a vacuum.

6. The apparatus of claim 1, wherein the apparatus includes a fiber bundle configured to split the laser into a plurality of fibers before the laser enters the first cell.

7. The apparatus of claim 6, wherein the apparatus includes an additional fiber bundle configured to:
bundle the plurality of fibers after the laser exits the first cell; and
re-split the bundled fibers before the laser enters the second cell.

8. A method for single ion addressing, comprising:
shuttering a laser using a first cell; and
aligning the shuttered laser to an ion in an ion trap using a second cell such that the ion fluoresces light and/or performs a quantum operation.

9. The method of claim 8, wherein the method includes preparing a state of the laser before shuttering the laser.

10. The method of claim 9, wherein the method includes preparing the state of the laser using an electro-optic modulator.

11. The method of claim 8, wherein the method includes shuttering the laser using an acousto-optic modulator of the first cell.

12. The method of claim 8, wherein the method includes aligning the shuttered laser to the ion in the ion trap using a lens of the second cell and a mirror of the second cell.

13. The method of claim 8, wherein the method includes aligning the shuttered laser to an additional ion in an additional ion trap using the second cell such that the additional ion fluoresces light and/or performs a quantum operation.

14. The method of claim 13, wherein:
aligning the shuttered laser to the ion in the ion trap includes aligning a first component of the shuttered laser to the ion in the ion trap; and
aligning the shuttered laser to the additional ion in the additional ion trap includes aligning a second component of the shuttered laser to the additional ion in the additional ion trap.

15. The method of claim 13, wherein the method includes detecting the light fluoresced from only a single one of the ion and the additional ion at a time.

16. The method of claim 8, wherein:
shuttering the laser includes shuttering a laser beam emitted by a single laser; and
aligning the shuttered laser to the ion in the ion trap includes aligning the shuttered laser beam emitted by the single laser to the ion in the ion trap such that the ion fluoresces light and/or performs a quantum operation when the ion is illuminated by the shuttered laser beam emitted by the single laser.

17. An apparatus for single ion addressing, comprising:
a first cell configured to:
set a frequency and a polarization of a laser; and
shutter the laser; and
a second cell inside a vacuum and configured to:
align the shuttered laser to an ion in an ion trap such that the ion fluoresces light and/or performs a quantum operation; and
receive the light fluoresced from the ion.

18. The apparatus of claim 17, wherein the apparatus includes a third cell configured to:
receive the light fluoresced from the ion from the second cell; and
detect the light fluoresced from the ion.

19. The apparatus of claim 17, wherein the first cell is outside the vacuum.

20. The apparatus of claim 17, wherein the second cell is configured to terminate the shuttered laser after the shuttered laser is aligned to the ion in the ion trap.

* * * * *